United States Patent
Lelkes et al.

(10) Patent No.: US 9,744,262 B2
(45) Date of Patent: Aug. 29, 2017

(54) ALIMENTARY PROTEIN-BASED SCAFFOLDS (APS) FOR WOUND HEALING, REGENERATIVE MEDICINE AND DRUG DISCOVERY

(71) Applicant: DREXEL UNIVERSITY, Philadelphia, PA (US)

(72) Inventors: Peter I. Lelkes, Cherry Hill, NJ (US); Dara L. Woerdeman, Merion Station, PA (US); Leko Lin, Plainsboro, NJ (US); Anat Katsir, Wynnewood, PA (US)

(73) Assignee: DREXEL UNIVERSITY, Philadelphia, PA (US)

( * ) Notice: Subject to any disclaimer, the term of this patent is extended or adjusted under 35 U.S.C. 154(b) by 0 days.

(21) Appl. No.: 14/301,672

(22) Filed: Jun. 11, 2014

(65) Prior Publication Data
US 2014/0294786 A1 Oct. 2, 2014

Related U.S. Application Data

(62) Division of application No. 12/525,803, filed as application No. PCT/US2008/001936 on Feb. 14, 2008, now Pat. No. 8,790,921.

(60) Provisional application No. 60/889,782, filed on Feb. 14, 2007.

(51) Int. Cl.
| | |
|---|---|
| *A61K 36/48* | (2006.01) |
| *A61L 27/24* | (2006.01) |
| *A61L 27/38* | (2006.01) |
| *A61L 27/22* | (2006.01) |
| *A61L 27/36* | (2006.01) |
| *A61L 27/60* | (2006.01) |

(52) U.S. Cl.
CPC .............. *A61L 27/24* (2013.01); *A61K 36/48* (2013.01); *A61L 27/227* (2013.01); *A61L 27/3637* (2013.01); *A61L 27/3804* (2013.01); *A61L 27/60* (2013.01)

(58) Field of Classification Search
CPC .......................... A61L 27/3637; A61K 36/899
See application file for complete search history.

(56) References Cited

U.S. PATENT DOCUMENTS

2002/0042128 A1 4/2002 Bowlin et al.
2004/0131663 A1* 7/2004 Walacavage ........... A61K 31/00
424/445

OTHER PUBLICATIONS

Yao et al., Fabrication of zein/hyaluronic acid fibrous membranes by electrospinning. J of Biomaterials Science Polymer Edition, vol. 18, No. 6 (Jan. 1, 2007) pp. 731-742.*
Cohen et al., Organization and adhesive properties of hyaluronan pericellular coat of chondrocytes and epithelial cells. Biophysical Journal, vol. 85, No. 3 (Sep. 2003) pp. 1996-2005.*
Lelkes et al., "Electrospinning of natural proteins for tissue engineering scaffolding." in: Reis et al., Natural-Based Polymers for Biomedical Applications (Cambridge, England, Woodhead Publishing Ltd., 2008), pp. 446-482.*
Jiang et al., Fabrication and characterization of zein-based nanofibrous scaffolds by an electrospinning method. Macromolecular Bioscience, vol. 7, No. 4 (Apr. 10, 2007) pp. 517-525.*
Torres-Giner et al., Characterization of the morphology and thermal properties of zein prolamine nanostructures obtained by electrospinning. Food Hydrocolloids, vol. 22, No. 4 (online Mar. 1, 2007) pp. 601-614.*
Woerdeman et al., Effects of hydroxyl groups versus physical entanglements behavior of wheat protein. Journal of Biobased Materials and Bioenergy, vol. 1 (2007) pp. 31-36.*
Yao et al., "Electrospinning and crosslinking of zein nanofiber mats," *Journal of Applied Polymer Science*, 2006, 103:380-385.
Silva et al., "Physical properties and biocompatibility of chitosan/soy blended membranes," *Journal of Materials Science: Materials*, 2005, 16:575-579.
Li et al., "Electrospun nanofibrous structure: A novel scaffold for tissue engineering," *Journal of Biomedical Materials Research*, 2002, 60(4):613-621.
Deans et al., "Mesenchymal stem cells: Biology and potential clinical uses," *Experimental Hematology*, 2000, 28(8):875-884.
Jin et al., "Electrospinning of Bombyx mori silk with poly(ethylene oxide)," *Biomacromolecules*, 2002, 3:1233-1239.
Woerdeman et al., "Electrospun fibers from Wheat protein: Investigation of the Interplay between Molecular Structure and the Fluid Dynamics of the Electrospinning Process," *Biomacromolecules*, 2005, 6:707-12.
Miyoshi et al., "Preparation of ultrafine fibrous zein membranes via electrospinning," *Polymer International*, 2005, 54:1187-90.

* cited by examiner

*Primary Examiner* — Kara Johnson
(74) *Attorney, Agent, or Firm* — Riverside Law LLP

(57) ABSTRACT

The invention provides engineered biomaterials derived from plant products. The engineered biomaterials are useful for biomedical applications. The engineered biomaterials are able to support the growth of animal calls.

1 Claim, 5 Drawing Sheets

ALIMENTARY PROTEIN-BASED SCAFFOLDS (APS) FOR WOUND HEALING, REGENERATIVE MEDICINE AND DRUG DISCOVERY

CROSS-REFERENCE TO RELATED APPLICATIONS

This application is a divisional application of U.S. application Ser. No. 12/525,803, filed Nov. 22, 2011, which is a U.S. national phase application filed under 35 U.S.C. §371claiming benefit to International Patent Application No. PCT/US2008/001936, filed Feb. 14, 2008, which in turn is entitled to priority under 35 U.S.C. §119(e) to U.S. Provisional Patent Application No. 60/889,782, filed Feb. 14, 2007, each of which application is hereby incorporated herein by reference in its entirety.

BACKGROUND OF THE INVENTION

Tissue engineering aims at restoring, maintaining or improving tissue function so as to extend and/or preserve the well being of an individual while decreasing the major cost burden on the medical community. These natural processes are occurring in nature using the 3D-structure of extracellular matrix (ECM) (the natural scaffold), which allows cells to grow, proliferate and differentiate within it. Artificial scaffolds have been made and used for therapeutic purposes (i.e. cardiac or skin implants) from natural polymers that desorb or degrade within the body.

The major challenge for tissue engineering researchers is to find materials and processing techniques that allow them to produce ECM mimicking scaffolds that promote cell growth and organization into a specific architecture, inducing differentiated cell function. ECM is a complex three-dimensional ultrastructure of proteins, proteoglycans and glycoproteins, used for cells growth in native tissue. In fact, there are many different types of ECMs for different parts of the body, for example, fibrous proteins are dominant material in tendon, polysaccharides are found largely existing in cartilage and so the forth. Collagens have been found to be the key proteins in ECM and also are the most ample proteins in the whole body.

ECM provides attachment sites and mechanical support for cells. The topology of ECM has been found to affect the cell structure, functionality and its physiological responsiveness. The geometry of the natural matrix was reported to modulate the cell polarity. Thyroid cells, smooth muscle cell and hepatocytes are different types of cells found to be affected by ECM's topology, with 3D-structures inducing cell differentiation more effectively than 2D configurations. The arrangement of ECM's configuration involves multiple length scales, layers and morphologies. However, although much is know about 3-D scaffolding of materials according to ECM topology to proliferate cell growth, satisfactory techniques and/or synthetic scaffolds have not been easily to construct.

In human skin, dermal fibroblasts secrete keratinocyte growth factor (KGF) and other growth factors that regulate keratinocyte proliferation and migration (Huang, et al., 2005, J Biomed Sci. 12(6): 855-67), while keratinocyte-derived cytokines may downregulate collagen synthesis by fibroblasts (Harrison, et al., 2006, Br J Dermatol. 154(3): 401-10). In large or non-healing wounds, this epithelial-mesenchymal interaction is obstructed by the lack of physical and biochemical cues for host cells to migrate and repair the wound site. Hence, an implantable platform is needed to provide an environment inductive to skin regeneration, by recruiting host cells and inducing them to secrete the appropriate signals and matrix components for repair.

Accordingly, there is a need for bioengineered tissue substitutes that can be custom-engineered to match the biomechanical, biochemical, and biological needs of the specific tissue or organ they are designed to replace.

BRIEF SUMMARY OF THE INVENTION

The present invention provides an electroprocessed composition comprising fibers of plant product derived biomaterials. In one embodiment, the invention provides an electrospun composition comprising fibers of plant product derived biomaterials.

In one embodiment, the plant product is from a plant selected from the group consisting of corn, wheat, potato, sorghums, tapioca, rice, arrow root, sago, soybean, pea, sunflower, peanut, gelatin, and any combination thereof In one embodiment, the plant product is soy protein isolate. In another embodiment, the plant product is corn zein.

In one embodiment, the composition is capable of supporting cell growth. In another embodiment, the composition is capable of supporting the maintenance of a differentiation state of a cell.

In one embodiment, the composition further comprises a cell. In another embodiment, the cell is genetically modified.

In one embodiment, the composition comprises a material selected from the group consisting of fibronectin, laminin, collagen, glycoprotein, thrombospondin, elastin, fibrillin, mucopolysaccharide, glycolipid, heparin sulfate, chondroitin sulfate, keratin sulfate, glycosaminoglycan, hyaluronic acid, proteoglycan, vitronectin, poly-D-lysine, polysaccharide, and any combination thereof.

In one embodiment, the composition comprises a synthetic material. In another embodiment, the synthetic material is selected from the group consisting of poly (epsilon-caprolactone) (PCL), poly (lactic acid) (PLA), poly (glycolic acid) (PGA), copolymers poly (lactide-co-glycolide) (PLGA), polyaniline, poly(ethylene oxide) (PEO), and any combination thereof.

The invention also provides a method of making a composition comprising a biomaterial derived from a plant product, wherein the biomaterial is electroprocessed to produce electroprocessed fibers. The method comprises obtaining a plant product and dissolving the plant product in a solvent to produce a protein solution; and subjecting the protein solution to electroprocessing to produced electroprocessed fibers.

In one embodiment, the step of electroprocessing is electrospinning; and the electroprocessed fibers are electrospun fibers.

In one embodiment, the plant product is from a plant selected from the group consisting of corn, wheat, potato, sorghums, tapioca, rice, arrow root, sago, soybean, pea, sunflower, peanut, gelatin, and any combination thereof.

In one embodiment, the plant product is soy protein isolate. In another embodiment, the soy protein isolate is blended with poly(ethylene oxide) (PEO).

In one embodiment, the plant product is corn zein.

In one embodiment, the biomaterial comprises a material selected from the group consisting of fibronectin, laminin, collagen, glycoprotein, thrombospondin, elastin, fibrillin, mucopolysaccharide, glycolipid, heparin sulfate, chondroitin sulfate, keratin sulfate, glycosaminoglycan, hyaluronic acid, proteoglycan, vitronectin, poly-D-lysine, polysaccharide, and any combination thereof.

In one embodiment, the biomaterial further comprises a synthetic material. In another embodiment, the synthetic material is selected from the group consisting of poly (epsilon-caprolactone) (PCL), poly (lactic acid) (PLA), poly (glycolic acid) (PGA), copolymers poly (lactide-co-glycolide) (PLGA), polyaniline, poly(ethylene oxide) (PEO), and any combination thereof.

In one embodiment, the solvent is selected from the group consisting of an organic solvent, an acid, a base, an alcohol, and any combination thereof. In another embodiment, the solvent is selected from the group consisting of 1,1,1,3,3,3-hexafluoro-2-propanol (HFP) and glacial acetic acid.

The invention also provides a method of culturing a cell with an engineered scaffold comprising a biomaterial derived from a plant product, wherein the biomaterial is electroprocssed to produce electroprocessed fibers. The method comprises contacting cells with the engineered scaffold in the presence of a culture medium.

In one embodiment, the culturing of a cell with a scaffold produces a target tissue substitute. In another embodiment, the cell is selected from the group consisting of stem cells, muscle cells, endothelial cells, nerve cells, bone cells, heart cells, epithelial cells, fibroblasts, and mixtures thereof.

The invention also provides a method of delivering an agent to a mammal. The method comprises administering an engineered scaffold comprising a biomaterial derived from a plant product, wherein the biomaterial is electroprocessed to produce electroprocessed fibers, further wherein the scaffold comprises an agent.

In one embodiment, the agent agent is a cell. In another embodiment, the agent is selected from the group consisting of an extracellular matrix component, a growth factor, a differentiation factor, and combinations thereof. In another embodiment, the agent is selected from the group consisting of a chemical agent, a pharmaceutical, a peptide, a nucleic acid, and any combination thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIG. 1A is an image of fiber morphology of electrospun fibers of 5% SPI, 0.025% PEO blended fiber; FIG. 1B is an image of fiber morphology electrospun fibers of 6% SPI, 0.025% PEO blended fiber; FIG. 1C is an image of fiber morphology of electrospun fibers of 7% SPI, 0.025% blended fiber; FIG. 1D is an image of fiber morphology of electrospun fibers of 8% SPI, 0.025% blended fiber; FIG. 1E is an image of fiber morphology of electrospun fibers of 5% SPI, 0.05% PEO blended fiber; FIG. 1F is an image of fiber morphology of electrospun fibers of 6% SPI, 0.05% PEO blended fiber; FIG. 1G is an image of fiber morphology of electrospun fibers of 7% SPI, 0.05% PEO blended fiber; and FIG. 1H is an image of fiber morphology of electrospun fibers of 8% SPI, 0.05% PEO blended fiber.

FIG. 5, comprising FIG. 5A is an image depicting the growth of human dermal fibroblasts on electrospun fibers of 5% SPI, 0.05% PEO blended fiber; FIG. 5B is an image depicting the growth of human dermal fibroblasts on electrospun fibers of 6% SPI, 0.05% PEO blended fiber; FIG. 5C is an image depicting the growth of human dermal fibroblasts on electrospun fibers 7% SPI, 0.05% PEO blended fiber; FIG. 5D is an image depicting the growth of human dermal fibroblasts on electrospun fibers 8% SPI, 0.05% PEO blended fiber; FIG. 5E is an image depicting the growth of human dermal fibroblasts on electrospun fibers of 8% gelatin; FIG. 5F is an image depicting the growth of human dermal fibroblasts on electrospun fibers of 20% PLGA.

DETAILED DESCRIPTION OF THE INVENTION

Figure 1A:
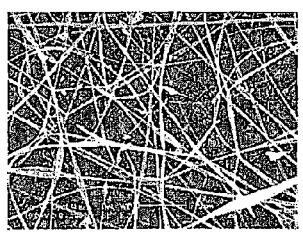
FIGS. 1A-1H, is a series of images demonstrating the general trend of increase in fiber width or diameter corresponds with increasing protein concentration.
Figure 1B:
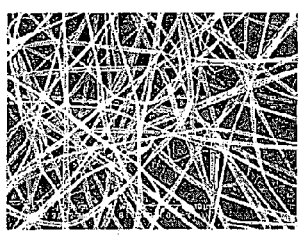
Figure 1C:
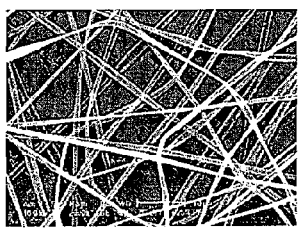
Figure 1D:
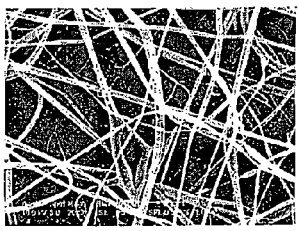
Figure 1E:
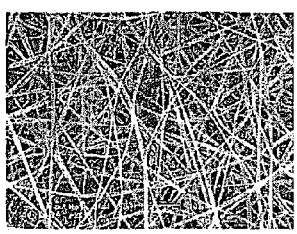
Figure 1F:
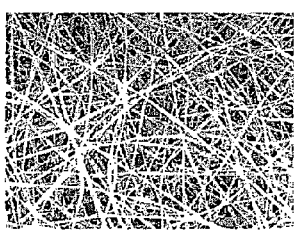
Figure 1G:
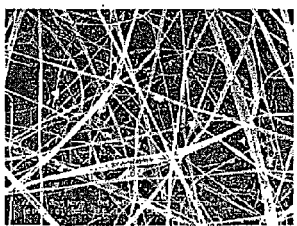
Figure 1H:
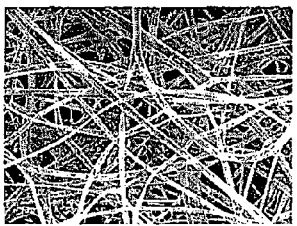

The present invention is partly based on the discovery that plant-derived proteins can be used as a source of biomaterials for tissue engineering purposes. In one aspect, the invention includes a scaffold produced from a plant product, wherein the scaffold is able to support the growth of animal calls. In another aspect, the scaffold mimics natural extracellular matrix (ECM).

The invention includes the use of any products obtained from alimentary plants. Non-limiting examples of alimentary plants include, but are not limited to corn, wheat, potato, sorghums, tapioca, rice, arrow root, sago, soybean, pea, sunflower, peanut, gelatin.

In one embodiment of the invention, the scaffold is produced by an electrospinning process. In certain aspects, the electrospinning process of the present invention uses a one-step electrospinning technique and therefore is easy to use and is cost effective.

The invention also provides fibers and nanofibrous biocompatible matrix electrospun from a blend of synthetic polymers and natural proteins. The matrix can be used as tissue engineering scaffold and implanted into the body to replace/repair damaged/non-functional tissues. The particular blends provide a unique mix of mechanical and physical properties that facilitates cell penetration and proliferation within the scaffolds without crosslinking.

Electrospinning provides an efficient approach to fabricating scaffolds derived from proteins of plants for tissue engineering. The advantage of this scaffold is the accessibility of proteinaceous products from plants. The novel approach to generating composite scaffolds of plant-based biomaterials affords tissue engineers the ability to meet all necessary design criteria in fabricating scaffolds for a given application, such as drug delivery, wound healing, regenerative medicine, and the like.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Laboratory Press, Cold Spring Harbor, N.Y., and Ausubel et al., 2002, Current Protocols in Molecular Biology, John Wiley & Sons, New York, N.Y.), which are provided throughout this document.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent based on the context in which it is used.

As used herein, "administering" refers to at least oral administration, administration as a suppository, topical contact, intravenous, intraperitoneal, intramuscular, intralesional, intranasal or subcutaneous administration, or the implantation of a slow-release device e.g., a mini-osmotic pump, to the subject.

The term "attached," as used herein encompasses interaction including, but not limited to, covalent bonding, ionic bonding, chemisorption, physisorption and combinations thereof.

The term "biomolecule" or "bioorganic molecule" refers to an organic molecule typically made by living organisms. This includes, for example, molecules comprising nucleotides, amino acids, sugars, fatty acids, steroids, nucleic acids, polypeptides, peptides, peptide fragments, carbohydrates, lipids, and combinations of these (e.g., glycoproteins, ribonucleoproteins, lipoproteins, or the like).

The term "differentiation factor", as used herein, refers to a molecule that induces a stem cell or progenitor cell to commit to a particular specialized cell type.

"Extracellular matrix" or "matrix" refers to one or more substances that provide substantially the same conditions for supporting cell growth as provided by an extracellular matrix synthesized by feeder cells. The matrix may be provided on a substrate. Alternatively, the component(s) comprising the matrix may be provided in solution. Components of an extracellular matrix can include laminin, collagen and fibronectin.

The term "extracellular matrix component", as used herein, can include a member selected from laminin, collagen, fibronectin and elastin.

The term "electroprocessing" shall be defined broadly to include all methods of electrospinning, electrospraying, electroaerosoling, and electrosputtering of materials, combinations of two or more such methods, and any other method wherein materials are streamed, sprayed, sputtered or dripped across an electric field and toward a target. The electroprocessed material can be electroprocessed from one or more grounded reservoirs in the direction of a charged substrate or from charged reservoirs toward a grounded target. The term electroprocessing is not limited to the specific examples set forth herein, and it includes any means of using an electrical field for depositing a material on a target.

As used herein, the term "electrospinning," also known as "electrostatic spinning," includes various processes for forming polymeric fibers including nanofibers and microfibers by expressing a liquid polymeric formulation through a capillary, syringe or similar implement (referred to herein as a flow tube) under the influence of an electrostatic field and collecting the so-formed fibers on a target.

"Electroaerosoling" means a process in which droplets are formed from a solution or melt by streaming an electrically charged polymer solution or melt through an orifice.

A "growth environment" is an environment in which stem cells will proliferate in vitro. Features of the environment include the medium in which the cells are cultured, and a supporting structure (such as a substrate on a solid surface) if present.

"Growth factor" refers to a substance that is effective to promote the growth of cells. Growth factors include, but are not limited to, basic fibroblast growth factor (bFGF), acidic fibroblast growth factor (aFGF), epidermal growth factor (EGF), insulin-like growth factor-I (IGF-T), insulin-like growth factor-II (IGF-II), platelet-derived growth factor-AB (PDGF), vascular endothelial cell growth factor (VEGF), activin-A, bone morphogenic proteins (BMPs), insulin, cytokines, chemokines, morphogens, neutralizing antibodies, other proteins, and small molecules.

"Hydrogel" refers to a water-insoluble and water-swellable cross-linked polymer that is capable of absorbing at least 3 times, preferably at least 10 times, its own weight of a liquid. "Hydrogel" can also refer to a "thermo-responsive polymer" as used herein.

As used herein, "scaffold" refers to a structure, comprising a biocompatible material, that provides a surface suitable for adherence and proliferation of cells. A scaffold may further provide mechanical stability and support. A scaffold may be in a particular shape or form so as to influence or delimit a three-dimensional shape or form assumed by a population of proliferating cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

The term "isolated" refers to a material that is substantially or essentially free from components, which are used to produce the material. The lower end of the range of purity for the compositions is about 60%, about 70% or about 80% and the upper end of the range of purity is about 70%, about 80%, about 90% or more than about 90%.

As used here, "biocompatible" refers to any material, which, when implanted in a mammal, does not provoke an adverse response in the mammal. A biocompatible material, when introduced into an individual, is not toxic or injurious to that individual, nor does it induce immunological rejection of the material in the mammal.

As used herein, a "graft" refers to a cell, tissue or organ that is implanted into an individual, typically to replace, correct or otherwise overcome a defect. A graft may further comprise a scaffold. The tissue or organ may consist of cells that originate from the same individual; this graft is referred to herein by the following interchangeable terms: "autograft", "autologous transplant", "autologous implant" and "autologous graft". A graft comprising cells from a genetically different individual of the same species is referred to herein by the following interchangeable terms: "allograft", "allogeneic transplant", "allogeneic implant" and "allogeneic graft". A graft from an individual to his identical twin is referred to herein as an "isograft", a "syngeneic transplant", a "syngeneic implant" or a "syngeneic graft". A "xenograft", "xenogeneic transplant" or "xenogeneic implant" refers to a graft from one individual to another of a different species.

As used herein, the terms "tissue grafting" and "tissue reconstructing" both refer to implanting a graft into an individual to treat or alleviate a tissue defect, such as a lung defect or a soft tissue defect.

As used herein, to "alleviate" a disease, defect, disorder or condition means reducing the severity of one or more symptoms of the disease, defect, disorder or condition.

As used herein, to "treat" means reducing the frequency with which symptoms of a disease, defect, disorder, or adverse condition, and the like, are experienced by a patient.

As used herein, a "therapeutically effective amount" is the amount of a composition of the invention sufficient to provide a beneficial effect to the individual to whom the composition is administered.

As used herein, the term "growth medium" is meant to refer to a culture medium that promotes growth of cells. A growth medium will generally contain animal serum. In some instances, the growth medium may not contain animal serum.

"Differentiation medium" is used herein to refer to a cell growth medium comprising an additive or a lack of an additive such that a stem cell, fetal pulmonary cell or other such progenitor cell, that is not fully differentiated, develops into a cell with some or all of the characteristics of a differentiated cell when incubated in the medium.

An "isolated cell" refers to a cell which has been separated from other components and/or cells which naturally accompany the isolated cell in a tissue or mammal.

As used herein, a "substantially purified" cell is a cell that is essentially free of other cell types. Thus, a substantially purified cell refers to a cell which has been purified from other cell types with which it is normally associated in its naturally-occurring state.

"Expandability" is used herein to refer to the capacity of a cell to proliferate, for example, to expand in number or, in the case of a population of cells, to undergo population doublings.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cell, and the like.

As used herein, "tissue engineering" refers to the process of generating tissues ex vivo for use in tissue replacement or reconstruction. Tissue engineering is an example of "regenerative medicine," which encompasses approaches to the repair or replacement of tissues and organs by incorporation of cells, gene or other biological building blocks, along with bioengineered materials and technologies.

As used herein "endogenous" refers to any material from or produced inside an organism, cell or system.

"Exogenous" refers to any material introduced into or produced outside an organism, cell, or system.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

An "isolated nucleic acid" refers to a nucleic acid segment or fragment which has been separated from sequences which flank it in a naturally-occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The phrase "under transcriptional control" or "operatively linked" as used herein means that the promoter is in the correct location and orientation in relation to the polynucleotides to control RNA polymerase initiation and expression of the polynucleotides.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a cell substantially only if the cell is a cell of the tissue type corresponding to the promoter.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (i.e., naked or contained in liposomes) and viruses that incorporate the recombinant polynucleotide.

The term "patient" as used herein includes human and veterinary subjects.

As used herein, "wound healing" is intended to include all disorders characterized by any disease, disorder, syndrome, anomaly, pathology, or abnormal condition of the skin and/or underlying connective tissue, e.g., skin wounds following surgery, skin abrasions caused my mechanical trauma, caustic agents or burns, cornea following cataract surgery or corneal transplants, mucosal epithelium wounds following infection or drug therapy (e.g., respiratory, gastrointestinal, genitourinary, mammary, oral cavity, ocular tissue, liver and kidney), diabetic wounds, skin wounds following grafting, and regrowth of blood vessels following angioplasty.

DESCRIPTION OF THE INVENTION

The present invention provides a method of using plant-derived proteins as a source of biomaterials for tissue engineering purposes. In one aspect, the invention includes a scaffold produced from a plant product, wherein the scaffold is able to support the growth of animal calls. In another aspect, the scaffold mimics natural extracellular matrix (ECM).

The invention includes the use of any proteinaceous products obtained from alimentary plants. Non-limiting examples of alimentary plants include, but are not limited to corn, wheat, potato, sorghums, tapioca, rice, arrow root, sago, soybean, pea, sunflower, peanut, gelatin. The invention provides a means of generating biomaterials from products and the biomaterials can be used as a scaffold in tissue engineering, drug delivery, drug discovery, therapy, and other research purposes.

Composition

The invention is based on the discovery that plant products such as soy protein and corn zein can be used to produce a scaffold capable of supporting the growth of cells and therefore provides an alternative biodegradable composition for biomedical applications. However, the invention should not be limited to only soy and corn. Rather, the invention includes a novel method of using any natural product such as proteins obtained from alimentary products.

The possibility to modify both the chemistry and the morphology of the natural alimentary materials (i.e., materials obtained from an alimentary plant) are also claimed in the present invention offering a series of approaches to make these natural alimentary materials suitable for many biomedical applications. These modifications aim to modulate the degradation time of the material varying its porosity and surface chemistry as well as to improve the material biocompatibility and mechanical properties.

By way of example, the following section describes a soybean-based scaffold. However, the invention should not be construed to be limited to a soybean-based scaffold. As used herein, the term "soy material" is defined as a material derived from soybeans. The term "soybean" refers to the species Glycine max, Glycine soja, or any species that is sexually cross compatible with Glycine max.

The term "soy protein isolate" as used herein is used in the sense conventional to the soy protein industry. For example, a soy protein isolate is a soy material having a protein content of at least 90% soy protein on a moisture free basis. "Isolated soy protein", as used in the art, has the same meaning as "soy protein isolate" as used herein and as used in the art. A soy protein isolate is formed from soybeans by removing the hull and germ of the soybean from the cotyledon, flaking or grinding the cotyledon and removing oil from the flaked or ground cotyledon, separating the soy protein and carbohydrates of the cotyledon from the cotyledon fiber, and subsequently separating the soy protein from the carbohydrates.

In one embodiment, the soy-based composition comprises a fibrous material containing soy protein and soy cotyledon fiber. The fibrous material generally comprises a defatted soy protein material and soy cotyledon fiber. The fibrous material is produced by extruding the soy protein material and soy cotyledon fiber. The fibrous material has a moisture content of from 6% to 80%. Moisture conditions employed in producing the fibrous material are low moisture fibrous material (6% to 35%) and high moisture fibrous material (50% to 80%). Additional ingredients may be extruded with the soy protein material and the soy cotyledon fiber such as wheat gluten and starch.

The soy protein isolate should not be a highly hydrolyzed soy protein isolate having a low molecular weight distribution since highly hydrolyzed soy protein isolates lack the protein chain length to properly form protein fibers in the process. Highly hydrolyzed soy protein isolates, however, may be used in combination with other soy protein isolates provided that the highly hydrolyzed soy protein isolate content of the combined soy protein isolates is less than 40% of the combined soy protein isolates, by weight.

The soy protein isolate utilized should have a water holding capacity sufficient to enable the protein in the isolate to form fibers upon extrusion. The water holding capacity of the soy protein isolate is a measure of the amount of swelling the protein undergoes when hydrated. The swelling of the protein should be sufficient to enable the protein to form intermolecular contacts to permit fiber formation to occur. The soy protein isolate used in the process of the invention preferably has a water holding capacity of at least 4.0 grams of water per gram of soy protein isolate (as is) at pH 7.0, and more preferably has a water holding capacity of at least 5.0 grams of water per gram of soy protein isolate (as is) at pH 7.0. The water holding capacity is determined by using the centrifuge method.

Non-highly hydrolyzed soy protein isolates having a water holding capacity of at least 4.0 grams of water per gram of soy protein isolate that are useful in the present invention are commercially available.

Soy protein isolates useful in the fibrous material may be produced from soybeans according to conventional processes in the soy protein manufacturing industry. Exemplary of such a process, whole soybeans are initially detrashed, cracked, dehulled, degermed, and defatted according to conventional processes to form soy flakes, soy flour, soy grits, or soy meal. The soybeans may be detrashed by passing the soybeans through a magnetic separator to remove iron, steel, and other magnetically susceptible objects, followed by shaking the soybeans on progressively smaller meshed screens to remove soil residues, pods, stems, weed seeds, undersized beans, and other trash. The detrashed soybeans may be cracked by passing the soybeans through cracking rolls. Cracking rolls are spiral-cut corrugated cylinders which loosen the hull as the soybeans pass through the rolls and crack the soybean material into several pieces. The cracked soybeans may then be dehulled by aspiration. The dehulled soybeans are degermed by shaking the dehulled soybeans on a screen of sufficiently small mesh size to remove the small sized germ and retain the larger cotyledons of the beans. The cotyledons are then flaked by passing the cotyledons through a flaking roll. The flaked cotyledons are defatted by extracting oil from the flakes by mechanically expelling the oil from the flakes or by contacting the flakes with hexane or other suitable lipophilic/hydrophobic solvent. The defatted flakes may be ground to form a soy flour, a soy grit, or a soy meal, if desired.

The defatted soy flakes, soy flour, soy grits, or soy meal is/are then extracted with an aqueous alkaline solution, typically a dilute aqueous sodium hydroxide solution having a pH of from 7.5 to 11.0, to extract protein soluble in an aqueous alkaline solution from insolubles. The insolubles are soy cotyledon fiber which is composed primarily of insoluble carbohydrates. An aqueous alkaline extract containing the soluble protein is subsequently separated from the insolubles, and the extract is then treated with an acid to lower the pH of the extract to around the isoelectric point of the soy protein, preferably to a pH of from 4.0 to 5.0, and most preferably to a pH of from 4.4 to 4.6. The soy protein precipitates from the acidified extract due to the protein's lack of solubility in an aqueous solution at or near its isoelectric point. The precipitated protein curd is then separated from the remaining extract. The separated protein may be washed with water to remove residual soluble carbohydrates and ash from the protein material. The separated protein is then dried using conventional drying means such as spray drying or tunnel drying to form a soy protein isolate.

Soy protein concentrate may be blended with the soy protein isolate to substitute for a portion of the soy protein isolate as a source of soy protein. Soy protein isolates, in general, have higher water holding capacity and form better fibers than soy protein concentrates. Therefore, the amount of soy protein concentrate substituted for soy protein isolate should be limited to an amount that will permit significant fiber formation in the extrudate. Preferably, if a soy protein concentrate is substituted for a portion of the soy protein isolate, the soy protein concentrate is substituted for up to 40% of the soy protein isolate by weight, at most, and more preferably is substituted for up to 30% of the soy protein isolate by weight.

Soy protein concentrates useful in the fibrous material are commercially available. Soy protein concentrates useful in the present invention may also be produced from soybeans according to conventional processes in the soy protein manufacturing industry. For example, defatted soy flakes, soy flour, soy grits, or soy meal produced as described above may be washed with aqueous ethanol (preferably 60% to 80% aqueous ethanol) to remove soluble carbohydrates from the soy protein and soy fiber. The soy protein and soy fiber containing material is subsequently dried to produce the soy protein concentrate. Alternatively, the defatted soy flakes, soy flour, soy grits, or soy meal may be washed with an aqueous acidic wash having a pH of from 4.3 to 4.8 to remove soluble carbohydrates from the soy protein and soy fiber. The soy protein and soy fiber containing material is subsequently dried to produce the soy protein concentrate.

The soy cotyledon fiber utilized in the fibrous material should effectively bind water when the mixture of soy protein material and soy cotyledon fiber are co-extruded. By binding water, the soy cotyledon fiber induces a viscosity gradient across the extrudate as the extrudate is extruded through a cooling die, thereby promoting the formation of protein fibers. To effectively bind water for the purposes of the process of the present invention, the soy cotyledon fiber should have a water holding capacity of at least 5.50 grams of water per gram of soy cotyledon fiber, and preferably the soy cotyledon fiber has a water holding capacity of at least 6.0 grams of water per gram of soy cotyledon fiber. It is also preferable that the soy cotyledon fiber has a water holding capacity of at most 8.0 grams of water per gram of soy cotyledon fiber.

The soy cotyledon fiber is a complex carbohydrate and is commercially available. Soy cotyledon fiber useful in the process of the present invention may also be produced according to conventional processes in the soy processing industry. For example, defatted soy flakes, soy flour, soy grits, or soy meal produced as described above may be extracted with an aqueous alkaline solution as described above with respect to the production of a soy protein isolate to separate the insoluble soy cotyledon fiber from the aqueous alkaline soluble soy protein and carbohydrates. The separated soy cotyledon fiber is then dried, preferably by spray drying, to produce a soy cotyledon fiber product. Soy cotyledon fiber is generally present in the fibrous material at from 1% to 8%, preferably at from 1.5% to 7.5% and most preferably at from 2% to 5% by weight on a moisture free basis.

The invention provides the use of soybean proteins for the generation of a biomaterial useful for engineering applications. When deprived from its oil component, soybean flour is a natural composite mainly constituted by proteins and carbohydrates. The production of the soybean milk from the ground flour and its processing into cheese of different texture by calcium solutions have been largely explored in food industry to provide healthy alimentary products. The disclosure presented herein demonstrate the production of a soy-based biomaterial that can be used to support the growth of cells and therefore demonstrate the applicability of soy in the biomedical field.

The invention provides fibers as well as nanofibrous biocompatible biomatrices electrospun from a natural product such as soy. In some instances, the natural product is blended with a synthetic polymer, such as poly(ethylene oxide) (PEO) to produce a tissue engineering scaffold. The particular blends provide a unique mix of mechanical and physical properties that facilitates cell penetration and proliferation within the scaffolds without crosslinking.

Methods of Making a Scaffold

The scaffolds of the invention can be produced in a variety of ways. In an exemplary embodiment, the scaffold can be produced by electrospinning. Electrospinning is an atomization process of a conducting fluid which exploits the interactions between an electrostatic field and the conducting fluid. When an external electrostatic field is applied to a conducting fluid (e.g., a semi-dilute polymer solution or a polymer melt), a suspended conical droplet is formed, whereby the surface tension of the droplet is in equilibrium with the electric field. Electrostatic atomization occurs when the electrostatic field is strong enough to overcome the surface tension of the liquid. The liquid droplet then becomes unstable and a tiny jet is ejected from the surface of the droplet. As it reaches a grounded target, the material can be collected as an interconnected web containing relatively fine, i.e. small diameter, fibers. The resulting films (or membranes) from these small diameter fibers have very large surface area to volume ratios and small pore sizes. A detailed description of electrospinning apparatus is provided in Zong, et al., 2002 Polymer 43: 4403-4412; Rosen et al., 1990 Ann Plast Surg 25: 375-87; Kim, K., Biomaterials 2003, 24: 4977-85; Zong, X., 2005 Biomaterials 26: 5330-8. After electrospinninng, extrusion and molding can be utilized to further fashion the polymers. To modulate fiber organization into aligned fibrous polymer scaffolds, the use of patterned electrodes, wire drum collectors, or post-processing methods such as uniaxial stretching has been successful. Zong, X., 2005 Biomaterials 26: 5330-8; Katta, P., 2004 Nano Lett 4: 2215-2218; Li, D., 2005 Nano Lett 5: 913-6.

The protein solution comprising a product derived from a plant can be produced in one of several ways. One method involves dissolving the subsequent plant product in an appropriate solvent. This process can be accomplished in a syringe assembly or it can be subsequently loaded into a syringe assembly. Another method involves purchasing commercially available polymer solutions or commercially available polymers and dissolving them to create polymer solutions. For example, poly(ethylene oxide) (PEO) can be purchased from Sigma (Sigma, St. Louis, Mo.), poly-L-lactide (PLLA) can be purchased from DuPont (Wilmington, Del.), poly(lactide-co-glycolide) can be purchased from Ethicon (Somerville, N.J.). Additional polymer scaffold components of the invention, such as cells and biomolecules, are also commercially available from suppliers.

The protein solution comprising a product derived from a plant used to form scaffold is first dissolved in a solvent. The solvent can be any solvent which is capable of dissolving the plant product and/or subunits thereof. Typical solvents include a solvent selected from N,N-Dimethyl formamide (DMF), tetrahydrofuran (THF), methylene chloride, dioxane, ethanol, hexafluoroisopropanol (HFIP), chloroform, 1,1,1,3,3,3-hexafluoro-2-propanol (HFP), glacial acetic acid, water, and combinations thereof.

The protein solution can optionally contain a salt which creates an excess charge effect to facilitate the electrospinning process. Examples of suitable salts include NaCl, $KH_2PO_4$, $K_2HPO_4$, $KIO_3$, KCl, $MgSO_4$, $MgCl_2$, $NaHCO_3$, $CaCl_2$ or mixtures of these salts.

The protein solution forming the conducting fluid preferably has a protein concentration in the range of about 1 to about 80 wt %, more preferably about 8 to about 60 wt %.

The electric field created in the electrospinning process preferably is in the range of about 5 to about 100 kilovolts (kV), more preferably about 10 to about 50 kV. The feed rate of the conducting fluid to the spinneret (or electrode) preferably is in the range of about 0.1 to about 1000 microliters/min, more preferably about 1 to about 250 microliters/min.

The single or multiple spinnerets sit on a platform which is capable of being adjusted, varying the distance between the platform and the grounded collector substrate. The distance can be any distance which allows the solvent to essentially completely evaporate prior to the contact of the polymer with the grounded collector substrate. In an exemplary embodiment, this distance can vary from 1 cm to 25 cm. Increasing the distance between the grounded collector substrate and the platform generally produces thinner fibers.

In electrospinning cases where a rotating mandrel is required, the mandrel is mechanically attached to a motor, often through a drill chuck. In an exemplary embodiment, the motor rotates the mandrel at a speed of between about 1 revolution per minute (rpm) to about 500 rpm. In an exemplary embodiment, the motor rotation speed of between about 200 rpm to about 500 rpm. In another exemplary embodiment, the motor rotation speed of between about 1 rpm to about 100 rpm.

Additional embodiments or modifications to the electrospinning process and apparatus are described herein.

The invention also includes combinations of natural materials, combinations of synthetic materials, and combinations of both natural and synthetic materials. Examples of combinations include, but are not limited to: blends of different types of collagen (e.g. Type I with Type II, Type I with Type III, Type II with Type III, etc.); blends of one or more types of collagen with fibrinogen, thrombin, elastin, PGA, PLA, and polydioxanone; and blends of fibrinogen with one or more types of collagen, thrombin, elastin, PGA, PLA, and polydioxanone.

The electroprocessed material of the present invention can result from the electroprocessing of natural materials, synthetic materials, or combinations thereof Examples include but are not limited to amino acids, peptides, denatured peptides such as gelatin from denatured collagen, polypeptides, proteins, carbohydrates, lipids, nucleic acids, glycoproteins, lipoproteins, glycolipids, glycosaminoglycans, and proteoglycans.

Some preferred materials to be electroprocessed are naturally occurring extracellular matrix materials and blends of naturally occurring extracellular matrix materials, including but not limited to collagen, fibrin, fibrinogen, thrombin, elastin, laminin, fibronectin, hyaluronic acid, chondroitin 4-sulfate, chondroitin 6-sulfate, dermatan sulfate, heparin sulfate, heparin, and keratan sulfate, and proteoglycans. Especially preferred materials for electroprocessing include collagen, fibrin, fibrinogen, thrombin, fibronectin, and combinations thereof. Some collagens that are used include but are not limited to collagen types I, II, III, IV, V, VI, VII, VIII, IX, X, XI, XII, XIII, XIV, XV, XVI, XVII, XVIII, and XIX. Some preferred collagens include types I, II, and III. These proteins may be in any form, including but not limited to native and denatured forms. Other preferred materials for electroprocessing are carbohydrates such as polysaccharides (e.g. cellulose and its derivatives), chitin, chitosan, alginic acids, and alginates such as calcium alginate and sodium alginate. These materials may be isolated from plant products, humans or other organisms or cells or synthetically manufactured. Some especially preferred natural materials for electroprocessing are collagen, fibrinogen, thrombin, fibrin, fibronectin, and combinations thereof. Also included are crude extracts of tissue, extracellular matrix material, extracts of non-natural tissue, or extracellular matrix materials (i.e. extracts of cancerous tissue), alone or in combination. Extracts of biological materials, including but are not limited to cells, tissues, organs, and tumors may also be electroprocessed.

Collagen and fibrinogen can each been electrospun to produce fibers having repeating, band patterns along the length of the fibers. These patterns are observable, for example with transmission electron microscopy, and are typical of those produced by natural processes. In some embodiments, the banded pattern observed in electrospun collagen fibers is the same as that produced by cells in vivo. In some embodiments, the banding pattern in electrospun fibrinogen is the same as that of fibrinogen found in normal clots formed in vivo. While not wishing to be bound by any particular theory, it is believed that the banding apparent along natural collagen fibers results from the helical pattern of the protein chains in the collagen, while the banding in fibrinogen in vivo results from close packing of individual fibrin molecules in a stacked configuration. In some of these embodiments, the compositions are composed of fibrous webs rather than networks characteristic of fibrin clots. Further, in some embodiments, electroprocessed fibrinogen is not soluble in water, unlike native fibrinogen.

The invention includes all natural or natural-synthetic hybrid compositions that result from the electroprocessing of any material. Materials that change in composition or structure before, during, or after electroprocessing are within the scope of the invention.

It is to be understood that these electroprocessed materials may be combined with other materials and/or substances in forming the compositions of the present invention. For example, in some embodiments an electroprocessed peptide is combined with an adjuvant to enhance immunogenicity when implanted subcutaneously. Electroprocessed materials in some embodiments are prepared at very basic or acidic pHs (for example, by electroprocessing from a solution having a specific pH) to accomplish the same effect. As another example, an electroprocessed matrix, containing cells, may be combined with an electroprocessed biologically compatible polymer and growth factors to stimulate growth and division of the cells in the electroprocessed matrix.

Synthetic materials electroprocessed for use in the scaffold include any materials prepared through any method of artificial synthesis, processing, isolation, or manufacture. The synthetic materials are preferably biologically compatible for administration in vivo or in vitro. Such polymers include but are not limited to the following: poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactic acid (PLA), polyglycolic acids (PGA), poly(lactide-co-glycolides) (PLGA), nylons, polyamides, polyanhydrides, poly(ethylene-co-vinyl alcohol) (EVOH), polycaprolactone, poly(vinyl acetate) (PVA), polyvinylhydroxide, poly(ethylene oxide) (PEO) and polyorthoesters or any other similar synthetic polymers that may be developed that are biologically compatible. Some preferred synthetic materials include PLA, PGA, copolymers of PLA and PGA, polycaprolactone, poly(ethylene-co-vinyl acetate), EVOH, PVA, and PEO. Polymers with cationic moieties are also preferred in some embodiments. Examples of such polymers include, but are not limited to, poly(allyl amine), poly(ethylene imine), poly(lysine), and poly(arginine). The polymers may have any molecular structure including, but not limited to, linear, branched, graft, block, star, comb and dendrimer structures. Matrices can be formed of electrospun fibers, electroaerosol, electrosprayed, or electrosputtered droplets, electroprocessed powders or particles, or a combination of the foregoing.

By selecting different natural and synthetic materials, or combinations thereof, many characteristics of the scaffold are manipulated. The properties of the matrix comprised of electroprocessed material and a substance may be adjusted. In addition, selection of materials for electroprocessing can affect the permanency of an implanted matrix. For example, many matrices made by electroprocessing fibrinogen or fibrin may degrade more rapidly while many matrices made of collagen are more durable and many other matrices made by electroprocessing materials are more durable still. Thus, for example, incorporation of durable synthetic polymers (e.g. PLA, PGA) increase the durability and structural strength of matrices electroprocessed from solutions of fibrinogen in some embodiments. Use of matrices made by electroprocessing natural materials such as proteins derived from corn, wheat, potato, sorghums, tapioca, rice, arrow root, sago, soybean, pea, sunflower, peanut, gelatin, and the like also minimize rejection or immunological response to an implanted matrix. Accordingly, selection of materials for electroprocessing and use in substance delivery is influenced by the desired use.

In one embodiment, a skin patch of material electroprocessed from fibrin, fibrinogen, fibronectin, collagen or a combination of one or more of these is combined with healing promoters, analgesics and or anesthetics and anti-rejection substances and applied to the skin and may subsequently dissolve into the skin. In another embodiment, an electroprocessed implant for delivery to bone may be constructed of materials useful for promoting bone growth, osteoblasts and hydroxyapatite, and may be designed to endure for a prolonged period of time. In embodiments in which the matrix contains substances that are to be released from the matrix, incorporating electroprocessed synthetic components, such as biocompatible substances, can modulate the release of substances from an electroprocessed composition. For example, layered or laminate structures can be used to control the substance release profile. Unlayered structures can also be used, in which case the release is controlled by the relative stability of each component of the construct. For example, layered structures composed of alternating electroprocessed materials are prepared by sequentially electroprocessing different materials onto a target. The outer layers are, for example, tailored to dissolve faster or slower than the inner layers. Multiple agents can be delivered by this method, optionally at different release rates. Layers can be tailored to provide a complex, multi-kinetic release profile of a single agent over time. Using combinations of the foregoing provides for release of multiple substances released, each with its own profile. Complex profiles are possible.

Natural components such as biocompatible substances can be used to modulate the release of electroprocessed materials or of substances from an electroprocessed composition. For example, a drug or series of drugs or other materials or substances to be released in a controlled fashion can be electroprocessed into a series of layers. In one embodiment, one layer is composed of electroprocessed fibrinogen plus a drug, the next layer PLA plus a drug, a third layer is composed of polycaprolactone plus a drug. The layered construct can be implanted, and as the successive layers dissolve or break down, the drug (or drugs) is released in turn as each successive layer erodes. In some embodiments, unlayered structures are used, and release is controlled by the relative stability of each component of the construct.

In some embodiments, the electroprocessed material itself may provide a therapeutic effect. Non-limiting examples of a material that has a therapeutic effect is electroprocessed fibrinogen, thrombin, fibrin, or combinations thereof. For example, thrombin converts fibrinogen to fibrin. Fibrin assists in arrest of bleeding (hemostasis). Fibrin is a component of the provisional matrix that is laid down during the early stages of healing and may also promote the growth of vasculature in adjacent region. In many ways fibrin is a natural healing promoter. In some embodiments, electroprocessed fibrinogen also assists in healing. When placed in contact with a wound of a patient, such an electroprocessed material provides the same healing properties as fibrin.

Method for Forming Matrices or Scaffolds

The biocompatible scaffold may be shaped using methods such as, for example, solvent casting, compression molding, filament drawing, meshing, leaching, weaving, foaming, electrospinning and coating. In solvent casting, a solution of one or more proteins in an appropriate solvent, is cast as a branching pattern relief structure. After solvent evaporation, a thin film is obtained. In compression molding, a polymer is pressed at pressures up to 30,000 pounds per square inch into an appropriate pattern. Filament drawing involves drawing from the molten polymer and meshing involves forming a mesh by compressing fibers into a felt-like material. In leaching, a solution containing two materials is spread into a shape close to the final form of the artificial organ. Next a solvent is used to dissolve away one of the components, resulting in pore formation. (See U.S. Pat. No. 5,514,378 to Mikos).

The scaffold may be shaped into any number of desirable configurations to satisfy any number of overall system, geometry or space restrictions. For example, in the use of the scaffold for bladder, urethra, valve, or blood vessel reconstruction, the matrix or scaffold may be shaped to conform to the dimensions and shapes of the whole or a part of the tissue. The scaffold may be shaped in different sizes and shapes to conform to the organs of differently sized patients. For bladders, the scaffold should be shaped such that after its biodegradation, the resulting reconstructed bladder may be collapsible when empty in a fashion similar to a natural bladder. The matrix or scaffold may also be shaped in other fashions to accommodate the special needs of the patient.

In one embodiment, the scaffolds are seeded with one or more populations of cells to form an artificial organ construct. The artificial organ construct can be autologous, where the cell populations are derived from the subject's own tissue, or allogenic, where the cell populations are derived from another subject within the same species as the patient. The artificial organ construct can also be xenogenic, where the different cell populations are derived form a mammalian species that is different from the subject. For example the cells can be derived from organs of mammals such as humans, monkeys, dogs, cats, mice, rats, cows, horses, pigs, goats and sheep.

Cells can be isolated from a number of sources, including, for example, biopsies from living subjects and whole-organ recover from cadavers. The isolated cells are preferably autologous cells, obtained by biopsy from the subject intended to be the recipient. For example, a biopsy of skeletal muscle from the arm, forearm, or lower extremities, or smooth muscle from the area treated with local anesthetic with a small amount of lidocaine injected subcutaneously, and expanded in culture. The biopsy can be obtained using a biopsy needle, a rapid action needle which makes the procedure quick and simple.

Cells may be isolated using techniques known to those skilled in the art. For example, the tissue or organ can be disaggregated mechanically and/or treated with digestive enzymes and/or chelating agents that weaken the connections between neighboring cells making it possible to disperse the tissue into a suspension of individual cells without appreciable cell breakage. Enzymatic dissociation can be accomplished by mincing the tissue and treating the minced tissue with any of a number of digestive enzymes either alone or in combination. These include but are not limited to trypsin, chymotrypsin, collagenase, elastase, and/or hyaluronidase, DNase, pronase and dispase. Mechanical disruption can also be accomplished by a number of methods including, but not limited to, scraping the surface of the organ, the use of grinders, blenders, sieves, homogenizers, pressure cells, or insonicators.

Preferred cell types include, but are not limited to, urothelial cells, mesenchymal cells, especially smooth or skeletal muscle cells, myocytes (muscle stem cells), fibroblasts, chondrocytes, adipocytes, fibromyoblasts, and ectodermal cells, including ductile and skin cells, hepotocytes, Islet cells, cells present in the intestine, and other parenchymal cells, osteoblasts and other cells forming bone or cartilage. In some cases, it may also be desirable to include nerve cells. In other cases, it mal be desirable to include stem cells.

Once the tissue has been reduced to a suspension of individual cells, the suspension can be fractionated into subpopulations from which the cells elements can be obtained. This also may be accomplished using standard techniques for cell separation including, but not limited to, cloning and selection of specific cell types, selective destruction of unwanted cells (negative selection), separation based upon differential cell agglutinability in the mixed population, freeze-thaw procedures, differential adherence properties of the cells in the mixed population, filtration, conventional and zonal centrifugation, centrifugal elutriation (counterstreaming centrifugation), unit gravity separation, countercurrent distribution, electrophoresis and fluorescence-activated cell sorting.

Cell fractionation may also be desirable, for example, when the donor has diseases such as cancer or metastasis of other tumors to the desired tissue. A cell population may be sorted to separate malignant cells or other tumor cells from normal noncancerous cells. The normal noncancerous cells, isolated from one or more sorting techniques, may then be used for organ reconstruction.

Isolated cells can be cultured in vitro to increase the number of cells available for coating the biocompatible scaffold. The use of allogenic cells, and more preferably autologous cells, is preferred to prevent tissue rejection. However, if an immunological response does occur in the subject after implantation of the artificial organ, the subject may be treated with immunosuppressive agents such as, cyclosporin or FK506, to reduce the likelihood of rejection. In certain embodiments, chimeric cells, or cells from a transgenic animal, can be coated onto the biocompatible scaffold.

Isolated cells may be transfected prior to coating with genetic material. Useful genetic material may be, for example, genetic sequences which are capable of reducing or eliminating an immune response in the host. For example, the expression of cell surface antigens such as class I and class II histocompatibility antigens may be suppressed. This may allow the transplanted cells to have reduced chance of rejection by the host. In addition, transfection could also be used for gene delivery.

Isolated cells can be normal or genetically engineered to provide additional or normal function. Methods for genetically engineering cells with retroviral vectors, polyethylene glycol, or other methods known to those skilled in the art can be used. These include using expression vectors which transport and express nucleic acid molecules in the cells. (See Goeddel; Gene Expression Technology: Methods in Enzymology 185, Academic Press, San Diego, Calif. (1990).

Vector DNA is introduced into prokaryotic or cells via conventional transformation or transfection techniques. Suitable methods for transforming or transfecting host cells can be found in Sambrook et al. (Molecular Cloning: A Laboratory Manual, 3nd Edition, Cold Spring Harbor Laboratory press (2001)), and other laboratory textbooks.

Seeding of cells onto the matrix or scaffold can be performed according to standard methods. For example, the seeding of cells onto polymeric substrates for use in tissue repair has been reported (see, e.g., Atala, A. et al., J. Urol. 148(2 Pt 2): 658-62 (1992); Atala, A., et al. J. Urol. 150 (2

Pt 2): 608-12 (1993)). Cells grown in culture can be trypsinized to separate the cells, and the separated cells can be seeded on the matrix. Alternatively, cells obtained from cell culture can be lifted from a culture plate as a cell layer, and the cell layer can be directly seeded onto the scaffold without prior separation of the cells.

In a preferred embodiment, in the range of 1 million to 700 50 million cells are suspended in medium and applied to each square centimeter of a surface of a scaffold. Preferably, between 1 million and 50 million cells, and more preferably, between 1 million and 10 million cells are suspended in media and applied to each square centimeter of a surface of a scaffold. The matrix or scaffold is incubated under standard culturing conditions, such as, for example, 37° C., 5% $CO_2$, for a period of time until the cells attached. However, it will be appreciated that the density of cells seeded onto the scaffold can be varied. For example, greater cell densities promote greater tissue regeneration by the seeded cells, while lesser densities may permit relatively greater regeneration of tissue by cells infiltrating the graft from the host. Other seeding techniques may also be used depending on the matrix or scaffold and the cells. For example, the cells may be applied to the matrix or scaffold by vacuum filtration. Selection of cell types, and seeding of cells onto a scaffold, will be routine to one of ordinary skill in the art in light of the teachings herein.

In one embodiment, the scaffold is seeded with one population of cells to form an artificial organ construct. In another embodiment, the matrix or scaffold is seeded on two sides with two different populations of cells. This may be performed by first seeding one side of the matrix or scaffold and then seeding the other side. For example, the scaffold may be placed with one side on top and seeded. Then the matrix or scaffold may be repositioned so that a second side is on top. The second side may then be seeded with a second population of cells. Alternatively, both sides of the matrix or scaffold may be seeded at the same time. For example, two cell chambers may be positioned on both sides (i.e., a sandwich) of the scaffold. The two chambers may be filled with different cell populations to seed both sides of the matrix or scaffold simultaneously. The sandwiched scaffold may be rotated, or flipped frequently to allow equal attachment opportunity for both cell populations. Simultaneous seeding may be preferred when the pores of the matrix or scaffold are sufficiently large for cell passage from one side to the other side. Seeding the scaffold on both sides simultaneously can reduce the likelihood that the cells would migrate to the opposite side.

In another embodiment, two separate scaffolds may be seeded with different cell populations. After seeding, the two matrices may be attached together to form a single matrix or scaffold with two different cell populations on the two sides. Attachment of the scaffolds to each other may be performed using standard procedures such as fibrin glue, liquid co-polymers, sutures and the like.

In order to facilitate cell growth on the scaffold of the present invention, the scaffold may be coated with one or more cell adhesion-enhancing agents. These agents include but are not limited collagen, laminin, and fibronectin. The scaffold may also contain cells cultured on the scaffold to form a target tissue substitute. The target tissue that may be formed using the scaffold of the present invention may be an arterial blood vessel, wherein an array of microfibers is arranged to mimic the configuration of elastin in the medial layer of an arterial blood vessel. In the alternative, other cells may be cultured on the scaffold of the present invention. These cells include, but are not limited to, cells cultured on the scaffold to form a blood vessel substitute, epithelial cells cultured on the scaffold to form epithelial tissue, muscle cells cultured on the scaffold to form muscle tissue, endothelial cells cultured on the scaffold to form endothelial tissue, skeletal muscle cells cultured on the scaffold to form skeletal muscle tissue, cardiac muscle cells cultured on the scaffold to form cardiac muscle tissue, collagen fibers cultured on the scaffold to form cartilage, interstitial valvular cells cultured on the scaffold to form valvular tissue and mixtures thereof.

Therapeutic Application

Grafting of scaffolds to an organ or tissue to be augmented can be performed according to the methods described in herein or according to art-recognized methods. The matrix or scaffold can be grafted to an organ or tissue of the subject by suturing the graft material to the target organ. Implanting a neo-organ construct for total organ replacement can be performed according to the methods described herein or according to art-recognized surgical methods. The scaffold is also useful for delivery of biologics, enzymes that activate drugs, protease inhibitors, and the like.

In one embodiment, the invention includes the use of the natural protein based scaffolds as a platform to direct wound healing by the induction of native skin fibroblasts and keratinocytes to populate the scaffolds and secrete appropriate matrix components. In some instances, the scaffold can also include desirable cells. For example, the scaffold can included cells that have the ability to express angiogenic growth factors and cytokines, secrete wound healing related cytokines, secrete collagen, and promote wound healing in vivo.

Scaffolds of the invention described can be useful for clinical and personal wound care and soft tissue regeneration. In one aspect of the invention, scaffold is used as a wound dressing or graft for external skin wounds. In a clinical setting, the scaffold can be used to treat wounds resulting from trauma, burns, ulcers, abrasions, lacerations, surgery, or other damage. Surgeons can use these grafts to cover and protect the wound area, to temporarily replace lost or damaged skin tissue, and to guide new tissue generation and wound healing into the damaged area. In a clinical setting, the scaffold may be secured to the wound area using sutures, adhesives, or overlaying bandages. The scaffold may be cut to match the size of the wound, or may overlap the wound edges.

In another aspect of the invention, the scaffold may be tailored for personal/home care by combining the sheet with an adhesive backing to create a scaffold bandage. An adhesive section can hold the scaffold in place on a wounded area and can be removed when the fibers degrade or fuse with the tissue. The scaffold sheet may also be secured with a liquid or gel adhesive.

In another aspect of the invention, scaffold sheets can be used as gauze to absorb fluid and protect large wounds. This scaffold gauze can be wrapped around a wounded area or secured with tape.

In another aspect of the invention, scaffold sheets can be used to treat internal soft tissue wounds such as wounds in the amniotic sac, ulcers in the gastrointestinal tract or mucous membranes, gingival damage or recession, internal surgical incisions or biopsies, etc. The scaffold grafts can be sutured or adhered into place to fill or cover the damaged tissue area.

The scaffold has numerous characteristics that are useful for wound healing. First, the polymer scaffolds described herein that include nanofibers are both nano-porous and breathable. They can prevent microbes and infectious particles from crossing through, but they allow air flow and moisture penetration which are critical in natural wound healing.

Second, the fibers in this invention are biodegradable, which allows for temporary wound coverage followed by eventual ingrowth of new tissue. The choice of material for scaffold wound dressings can be determined to match the natural tissue characteristics including mechanical strength and rate of degradation/tissue regeneration.

Third, the scaffolds may be embedded or conjugated with various factors which may be released upon degradation. These factors may include, but are not limited to epidermal growth factor (EGF), platelet derived growth factor (PDGF), basic fibroblast growth factor (bFGF), transforming growth factor-β (TGF-β), and tissue inhibitors of metalloproteinases (TIMP), which have been shown to be beneficial in wound healing. Additional wound healing factors such as antibiotics, bacteriocides, fungicides, silver-containing agents, analgesics, and nitric oxide releasing compounds can also be incorporated into the scaffold wound dressings or grafts.

Fourth, scaffold grafts for wound healing may be seeded with cells for faster tissue regeneration and more natural tissue structure. These cells may include, but are not limited to fibroblasts, keratinocytes, epithelial cells, endothelial cells, mesenchymal stem cells, and/or embryonic stem cells.

Fifth, the nano-scale architecture of the nanofibrous scaffolds closely mimics that of the extracellular matrix (ECM) of many common soft tissues. For example, the nano-scale fibers are structurally similar to collagen fibrils found in skin and other tissues. This architecture may prevent scar formation by providing an organized scaffold for cells to migrate into a wound. In this aspect of the invention, alignment of the scaffold is preferred to keep cells aligned and organized, rather than allowing them to arrange randomly as in the formation of scar tissue. Aligned scaffolds may be oriented with respect to a given axis of the wound to allow faster tissue ingrowth and wound coverage.

Scaffold alignment can also be used to closely match the architecture of natural tissue ECM. This may include fiber alignment in a single direction, criss-cross alignment in orthogonal directions, or more complicated fiber architecture. In this instance of the invention, the scaffold includes multiple layers of fibers with specific fiber orientation in each layer. Similarly, each individual scaffold layer may also contain a specific factor or cell type such as the ones listed previously. This allows for creation of polymer scaffolds that can closely match natural tissue architecture and composition. For example, a simple scaffold wound dressing or graft might include a single layer of aligned fibers. On the other hand, a more complex scaffold skin graft might include multiple aligned fiber sheets layered in a criss-cross pattern with fibroblasts in the bottom sheets and keratinocytes in the top sheet, as well as bFGF in the bottom sheets and an antimicrobial agent in the top sheet. Other such combinations are possible, depending on the specific needs of the patient.

In another embodiment, the scaffold can include a therapeutic agent. The therapeutic agent can be an anti-tumor agent including but not limited to a chemotherapeutic agent, an anti-cell proliferation agent or any combination thereof.

The invention should not limited to any particular chemotherapeutic agent. Rather, any chemotherapeutic agent can be linked to the antibodies of the invention. For example, any conventional chemotherapeutic agents of the following non-limiting exemplary classes are included in the invention: alkylating agents; nitrosoureas; antimetabolites; antitumor antibiotics; plant alkyloids; taxanes; hormonal agents; and miscellaneous agents.

An anti-cell proliferation agent can further be defined as an apoptosis-inducing agent or a cytotoxic agent. The apoptosis-inducing agent may be a granzyme, a Bcl-2 family member, cytochrome C, a caspase, or a combination thereof. Exemplary granzymes include granzyme A, granzyme B, granzyme C, granzyme D, granzyme E, granzyme F, granzyme G, granzyme H, granzyme I, granzyme J, granzyme K, granzyme L, granzyme M, granzyme N, or a combination thereof. In other specific aspects, the Bcl-2 family member is, for example, Bax, Bak, Bcl-Xs, Bad, Bid, Bik, Hrk, Bok, or a combination thereof.

In additional aspects, the caspase is caspase-1, caspase-2, caspase-3, caspase-4, caspase-5, caspase-6, caspase-7, caspase-8, caspase-9, caspase-10, caspase-11, caspase-12, caspase-13, caspase-14, or a combination thereof. In specific aspects, the cytotoxic agent is TNF-α, gelonin, Prodigiosin, a ribosome-inhibiting protein (RIP), Pseudomonas exotoxin, Clostridium difficile Toxin B, Helicobacter pylori VacA, Yersinia enterocolitica YopT, Violacein, diethylenetriaminepentaacetic acid, irofulven, Diptheria Toxin, mitogillin, ricin, botulinum toxin, cholera toxin, saporin 6, or a combination thereof.

The invention also encompasses tissue regeneration applications. The objective of the tissue regeneration therapy approach is to deliver high densities of repair-competent cells (or cells that can become competent when influenced by the local environment) to the defect site in a format that optimizes both initial wound mechanics and eventual neotissue production. The composition of the instant invention is particularly useful in methods to alleviate or treat lung tissue defects in individuals. Advantageously, the composition of the invention provides for improved lung tissue regeneration. Specifically, the tissue regeneration is achieved more rapidly as a result of the inventive composition.

The composition of the invention may be administered to an individual in need thereof in a wide variety of ways. Preferred modes of administration include intravenous, intravascular, intramuscular, subcutaneous, intracerebral, intraperitoneal, soft tissue injection, surgical placement, arthroscopic placement, and percutaneous insertion, e.g. direct injection, cannulation or catheterization. Most preferred methods result in localized administration of the inventive composition to the site or sites of tissue defect. Any administration may be a single application of a composition of invention or multiple applications. Administrations may be to single site or to more than one site in the individual to be treated. Multiple administrations may occur essentially at the same time or separated in time.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Alimentary Protein-Based Scaffold

The following experiments were designed to generate biomaterials that can be used as scaffolds for biomedical purposes, such as tissue engineering. The results presented herein demonstrate the feasibility of producing a scaffold using plant products as the starting material. The scaffolds were shown to support cell growth.

The materials and methods employed in these experiments are now described.

Materials and Methods

Preparation of Protein Solutions

Soy protein isolate (SPI) (obtained from Cargill Health and Food Technologies, Minneapolis, Minn.) was blended with poly(ethylene oxide) (PEO) (Sigma, St. Louis, Mo.) by first dissolving 0.5% (w/v) PEO in 1,1,1,3,3,3-hexafluoro-2-propanol (HFP) (Sigma) and adding appropriate volumes from this stock solution to 5, 6, 7, and 8% (w/v) SPI in HFP respectively. Blend solutions were left to stir at least 48 hours before electrospinning to ensure complete dissolution.

Corn zein was dissolved at 35%, 40% and 45% (w/v) in glacial acetic acid (Fisher Scientific) and left to stir at least 24 h before electrospinning.

Electrospinning of Protein Solutions

Fibers were electrospun by using a syringe pump (KD Scientific Single Syringe Infusion Pump, Fisher) to eject solution from a 3 mL syringe through an 18-gauge needle at a delivery rate of 0.8 to 1.0 mL/h, air gap distance of 15 cm, and accelerating voltage of 12 kV for SPI/PEO blend solutions. For zein solutions, delivery rate was 0.5 mL/h, air gap distance was 15 cm, and accelerating voltage was 20 kV. For cell culture specimens, 15 mm diameter glass coverslips were attached to a rectangular aluminum collector and fiber-coated coverslips were detached from the collector. For mats, fibers were collected directly onto the aluminum collector.

Measurement of Fiber Diameters

Glass coverslips coated with electrospun fibers were mounted onto metal stubs with carbon tape and sputter-coated for 30 sec with platinum and palladium prior to visualization in an environmental scanning electron microscope (ESEM, XL-30 Environmental SEM-FEG). Images were taken of different areas at 2000× original magnification and measurements taken on UTHSCSA ImageTool 3.0 software (n=100 for each specimen).

Dry samples were mounted as spun. To investigate the degree of swelling with hydration over time, samples of 6% SPI/0.05% PEO and 40% zein were immersed in Dulbecco's Modified Eagle's Medium (DMEM) supplemented with 10% fetal bovine serum (FBS), 1X phosphate buffered saline (PBS) solution without calcium and magnesium, and tissue culture grade water (Mediatech Inc., Herndon, Va.) separately for 2 h, 24 h and 72 h. At these time points, samples were removed with forceps and rinsed five times in fresh tissue culture grade water before placing in a hybridization oven overnight at 37° C.

Characterization of Mechanical Properties

Mats were electrospun and cut into rectangular pieces and tensile tested using the Instron 5564 in dry and hydrated states. For hydrated state, samples were immersed in DMEM supplemented with 10% FBS for at least 2 h to simulate a physiological situation where proteases would be present. Samples were tested at a gauge length of 15 mm on a 10 N load cell. Crosshead speed was 1 mm/min for dry samples and 10 mm/min for wet samples. The test was stopped at specimen break or a predetermined amount of strain, whichever occurred first. Young's modulus was calculated from the slope of the first linear region of the stress-strain curve.

Cell Culture

Primary human dermal fibroblasts (HDF), were cultured in DMEM with 4.5 g/L glucose supplemented with 10% FBS and 2.5% penicillin/streptomycin (10,000 I.U./mL penicillin, 10,000 µg/mL streptomycin solution, Mediatech Inc., Hemdon, Va.). Flasks were kept in sterile incubators at 37° C. and 5% $CO_2$, and culture medium was changed twice per week. At confluence, cells were detached from flasks using 0.25% trypsin/2.21 mM EDTA and centrifuged in complete medium prior to counting and using.

Alamar Blue Assay for Metabolic Activity

Fluorescence spectrophotometric reading was calibrated against cells grown on tissue culture polystyrene (TCP) inside a 24-well plate to determine the appropriate seeding density prior to seeding cells onto scaffolds Cells were seeded at a density of 30,000 per well in 200 µL volumes onto scaffolds in triplicate in a 24-well plate. For each scaffold, one was kept unseeded as a blank to compensate for the effect of scaffold material on the readings. Cells were also seeded onto scaffolds electrospun from 20% PLGA and 8% gelatin as synthetic and natural control materials respectively, and onto glass and TCP as controls for the entire experiment.

After allowing the cells to attach to the scaffolds for 1 h, medium with 10% (v/v) Alamar Blue (BD, Franklin Lakes, N.J.) was added to each well to a total volume of 0.5 mL. Plates were incubated at 37° C., 5% $CO_2$ for 3 hours before supernatant from each well was transferred to a 96-well plate in 200 µL volumes in duplicate. Alamar Blue fluorescence was read on a Cytofluor fluorescence spectrophotometer.

Visualization of Cell Morphology on Scaffolds

Morphology of cells was assessed using fluorescence microscopy and environmental scanning electron microscopy (ESEM). For fluorescence microscopy, cells were fixed in 3.8% paraformaldehyde (Fisher) for 10 minutes, washed three times with 1×PBS, and stained with 4 gig/mL Hoechst 33258 (bisBenzimide, Sigma) (BBZ) and 2 µg/mL TRITC-conjugated rhodamine phalloidin (phalloidin-tetramethyl-rhodamine B isothiocyanate, Sigma) in 1×PBS with 0.2% Triton-X100 for 15 minutes for nuclei and actin cytoskeleton, respectively. Samples were visualized on a Leica DMRX upright microscope. Prior to visualizing in the SEM, samples were fixed with 2.5% glutaraldehyde in PBS for 1 h at 4° C. washed three times with 1×PBS, and dehydrated with a gradient of ethanol at 15%, 30%, 50%, 75%, 85%, 90%, 95% and 100%. Dehydrated samples were dried using a critical point dryer, mounted onto stubs with carbon tape and sputter coated with platinum and palladium for 30 sec. Samples were visualized in the SEM chamber at an accelerating voltage of 10 kV and spot size 3.

The results of the experiments are now described.

Variation of Fiber Morphology with Solution Concentration

Figure 2:
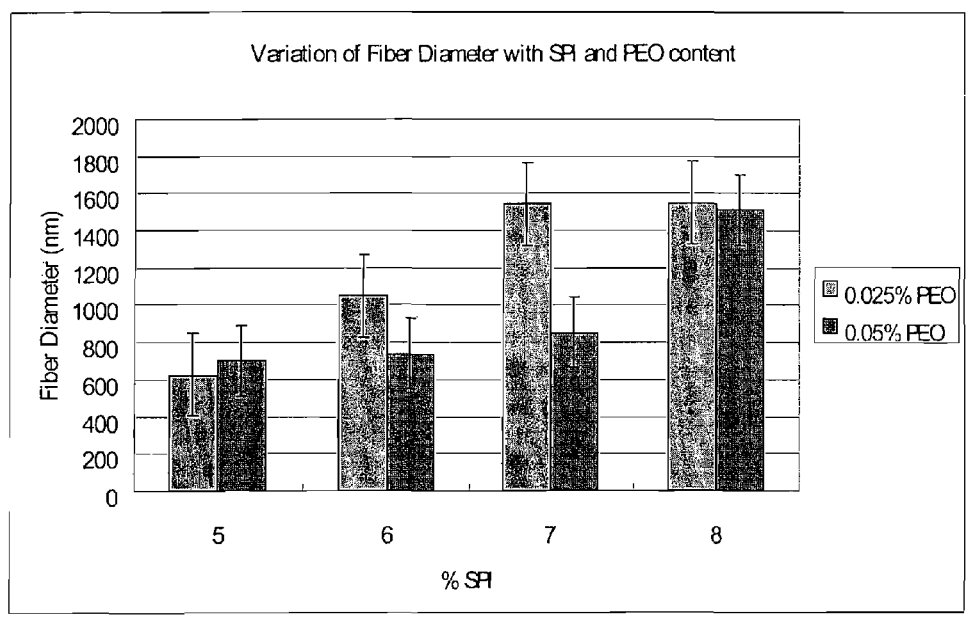
FIG. 2 is a chart demonstrating the general trend of increase in fiber width or diameter corresponds with increasing protein concentration of soy protein isolate (SPI) when blended with either 0.0025% PEO or 0.05% PEO.
Figure 3:
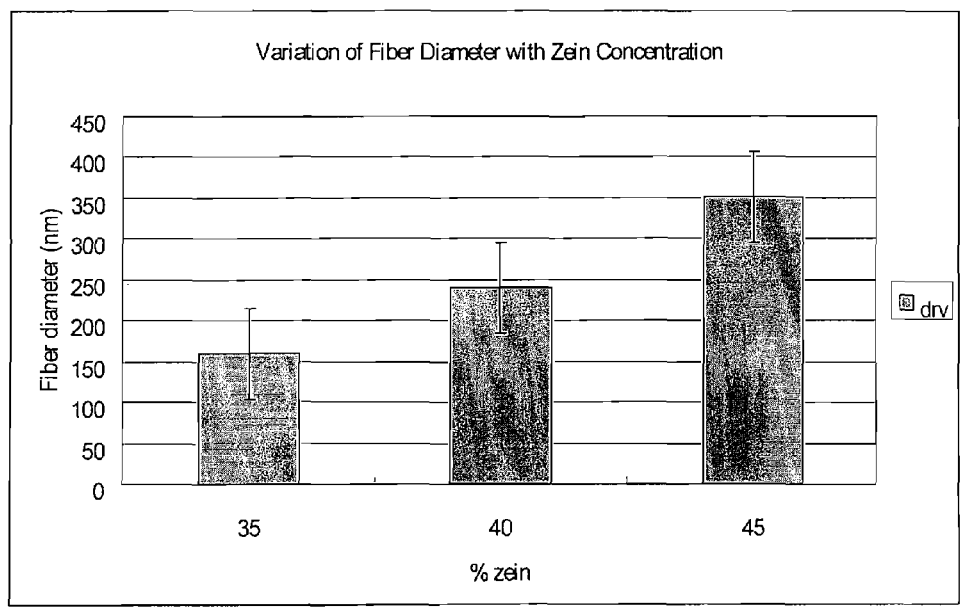
FIG. 3 is a chart demonstrating the general trend of increase in fiber width or diameter corresponds with increasing protein concentration of zein.

It was observed that SPI/PEO blend fibers as well as zein fibers followed the general trend of increasing in fiber width or diameter with increasing protein concentration. Surprisingly, lower content of PEO did not correlate to smaller fiber diameters, although the same volume of solution yielded less amount of electrospun fibers and the fibers were less uniform than those from solutions with higher amounts of PEO (See FIG. 1 and Table 1). The results presented in Table 1 are summarized in FIG. 2 and FIG. 3. Specifically, FIG. 2 demonstrates the variation of fiber diameter with SPI and PEO content; FIG. 3 demonstrates the variation of fiber diameter with zein concentration.

TABLE 1

Fiber width corresponding to protein concentration

| % SPI (0.05% PEO) | Width (mm) (n = 100) |
|---|---|
| 5 | 702 ± 201 |
| 6 | 738 ± 195 |
| 7 | 852 ± 373 |
| 8 | 1514 ± 447 |

| % zein | Diameter (nm) (n = 100) |
|---|---|
| 35 | 159 ± 18 |
| 40 | 236 ± 21 |
| 45 | 344 ± 27 |

Variation of Fiber Diameters with Hydration

Figure 4:
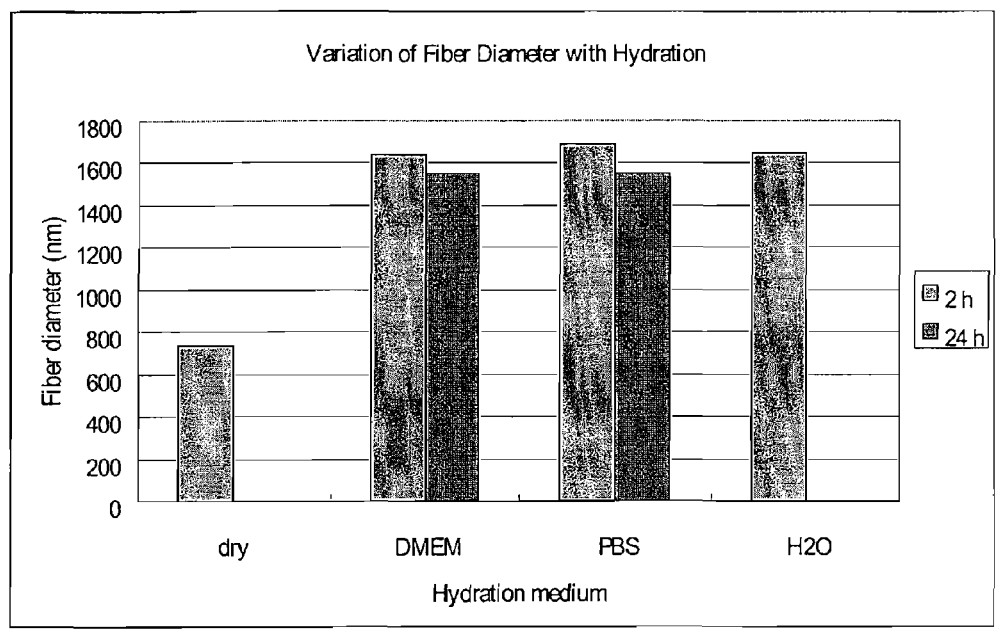
FIG. 4 is a chart depicting the variation of fiber diameter following hydration in DMEM, PBS, and water for 2 hours and 24 hours.
Figure 5A:
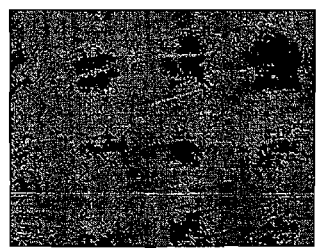
FIGS. 5A-5F, is a series of images demonstrating that the engineered scaffolds can support cell growth.
Figure 5D:
Figure 5B:
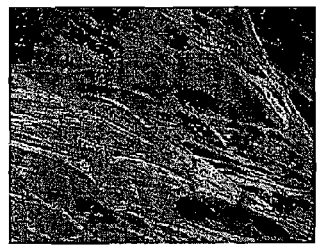
Figure 5E:
Figure 5C:
Figure 5F:
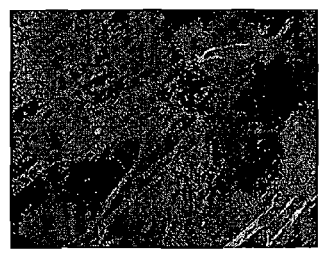

Fibers swelled to more than double their dry diameters after 2 hour of hydration in the case of SPI/PEO blend fibers. It was observed that swelling decrease after 24 h. It was observed that 6% SPI, 0.05% PEO fiber widths varied with hydration for 2 hour and 24 hour in DMEM, PBS and $H_2O$ (See Table 2 and FIG. 4). It was observed that 40% zein fiber widths varied with hydration for 2 hour and 24 hour in DMEM, PBS and $H_2O$ (Table 3).

TABLE 2

| 6% SPI, 0.05% PEO fiber diameter after hydration | | | | | | |
|---|---|---|---|---|---|---|
| | DMEM | | PBS | | H$_2$O | |
| Dry | 2 h | 24 h | 2 h | 24 h | 2 h | 24 h |
| 738 ± 195 | 1639 ± 291 | 1555 ± 236 | 1687 ± 456 | 1549 ± 254 | 1644 ± 363 | n/a |

TABLE 3

| Zein fiber diameter after hydration | | | | | | |
|---|---|---|---|---|---|---|
| | DMEM | | PBS | | H$_2$O | |
| Dry | 2 h | 24 h | 2 h | 24 h | 2 h | 24 h |
| 236 ± 21 | | | 342 ± 77 | | | |

Variation of Tensile Properties with Solution Concentration

SPI/PEO blend and zein scaffolds had similar mechanical properties and breaking mechanisms. Thinner dry specimens tended to break in a clean, brittle manner, while thicker specimens broke gradually as measured by the layers of fibers shearing apart (data not shown). Minimal difference was observed between mechanical properties of scaffolds with variation in the protein contents investigated. Hydrated samples had a Young's modulus of more than an order of magnitude lower than dry samples, with a correspondingly higher elasticity as determined by the higher strain at break. Some specimens did not break at 200% strain.

TABLE 4

| | Young's Modulus (MPa) | | Ultimate Tensile Strength (MPa) | | Strain at Break (%) | |
|---|---|---|---|---|---|---|
| | dry | hydrated | dry | hydrated | Dry | hydrated |
| SPI (%) | | | | | | |
| 5 | 26.47 ± 15.19 | 0.19 ± 0.19 | 0.92 ± 0.38 | 0.08 ± 0.04 | 10.14 ± 2.33 | 87.74 ± 18.03 |
| 6 | 26.60 ± 7.58 | 0.17 | 0.47 ± 0.14 | 0.079 | 4.44 ± 0.35 | 42.78 |
| 7 | 19.63 ± 4.43 | 0.19 ± 0.12 | 0.40 ± 0.11 | 0.12 ± 0.08 | 6.48 ± 1.01 | 67.51 ± 23.44 |
| 8 | 33.28 ± 12.12 | 0.14 | 0.75 ± 0.29 | 0.12 ± 0.01 | 5.22 ± 0.90 | 85.83 ± 5.11 |
| Zein (%) | | | | | | |
| 35 | 21.07 ± 6.21 | 0.75 ± 0.90 | 0.94 ± 0.39 | 0.39 ± 0.12 | | n/a |
| 40 | 11.63 ± 7.08 | 0.96 ± 0.27 | 0.51 ± 0.23 | 0.098 ± 0.015 | 12.14 ± 5.08 | 63.48 ± 11.47 |
| 45 | 21.59 ± 6.86 | 0.043 ± 0.012 | 0.40 ± 0.13 | 0.066 ± 0.025 | | |

SPI/PEO and Zein Scaffolds Support Cellular Growth and Proliferation

The next set of experiments were designed to assess whether the engineered scaffolds would support cell growth. Cells were seeded onto each respective scaffold (SPI/PEO and zein scaffold). Cells were also seeded onto scaffolds electrospun from 20% PLGA and 8% gelatin as synthetic and natural control materials, respectively. It was observed that human dermal fibroblasts grew able to grow on the engineered scaffolds (FIG. 5: a) 5% SPI, 0.05% PEO; b) 6% SPI, 0.05% PEO; c) 7% SPI, 0.05% PEO; d) 8% SPI, 0.05% PEO; e) 8% gelatin; f) 20% PLGA.)

Electrospun Scaffolds from Soy Protein Isolate (SPI)/Polyethylene Oxide (PEO) Blend and Zein for Skin Wound Healing Soy protein has long been exploited for use as industrial replacements for more expensive and less eco-friendly materials in textiles, plastics, adhesives and food applications. It has proven to be extremely versatile in that it can be formulated into films, powders, coatings, solids, gels or fibers depending on the property it is intended to provide or enhance. From a biological standpoint, soy protein was chosen as a possible biomaterial due to the bioactivity of individual peptides and isoflavones that may be metabolized by the body upon resorption of the scaffold. Despite its versatility, however, the use of soy protein as a biomaterial has seen slow growth due to processing limitations and poor mechanical properties. The results presented herein the successful generation of a biomaterial derived from soy bean that can support the growth of cells While soy protein isolate dissolved in bases and 1,1,1,3,3,3-hexafluoro-2-propanol (HFP), the solution did not yield fibers when electrospun, but only electrospraying behavior. Hence, a small amount of high molecular weight (1,000,000) synthetic polymer, poly (ethylene oxide) (PEO) was added in order to increase the chain entanglements, which resulted in yields of fibers.

Corn zein is an abundant byproduct of the bio-ethanol industry. The results presented herein demonstrate the successful generation of a biomaterial derived from Corn zein which was able to support growth of cells. Electrospinning of zein was optimized using glacial acetic acid as solvent to produce uniform, tubular nanofibers.

The results presented herein shown that SPI, with the addition of a small amount of PEO, can be formed into stable, hydrolysis-resistant submicron fibers that support cellular attachment, growth and proliferation. In addition, zein can be electrospun into stable nanofibers without the need for synthetic additives or crosslinking. No significant difference was observed in the mechanical properties and cellular behavior between SPI/PEO and zein nanofiber scaffolds.

Both SPI/PEO blend fibers as well as zein fibers remained stable in aqueous environments without external crosslinking. The results presented herein demonstrate that proteinaceous products from natural products otherwise referred to as "green" proteins provide a platform for directed wound healing by the induction of native skin fibroblasts and keratinocytes to populate the scaffolds and secrete appropriate matrix components and balanced signals. Although cell culture medium contains proteases that may degrade soy proteins and zein over time, the observation of a more rapid degradation of the scaffolds in medium compared to other aqueous solutions such as PBS and water over 8 days did not occur. Without wishing to be bound by any particular theory, it is believed that this observation was due to the protective or plasticizing effect of the serum in the medium.

The results presented herein demonstrate that products derived from alimentary plants, such as soybean and corn amongst other things, provide a platform for skin regeneration with the advantages of remaining stable without further crosslinking. The results presented herein describes a novel class of biomaterials.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating a wound in a subject, the method comprising contacting an electroprocessed composition comprising fibers of a soy protein isolate-derived biomaterial and a synthetic polymer to the wound of a subject in need thereof.

* * * * *